June 5, 1945. A. F. ETTER Plant Pat. 658
CRAB APPLE TREE
Filed June 23, 1944
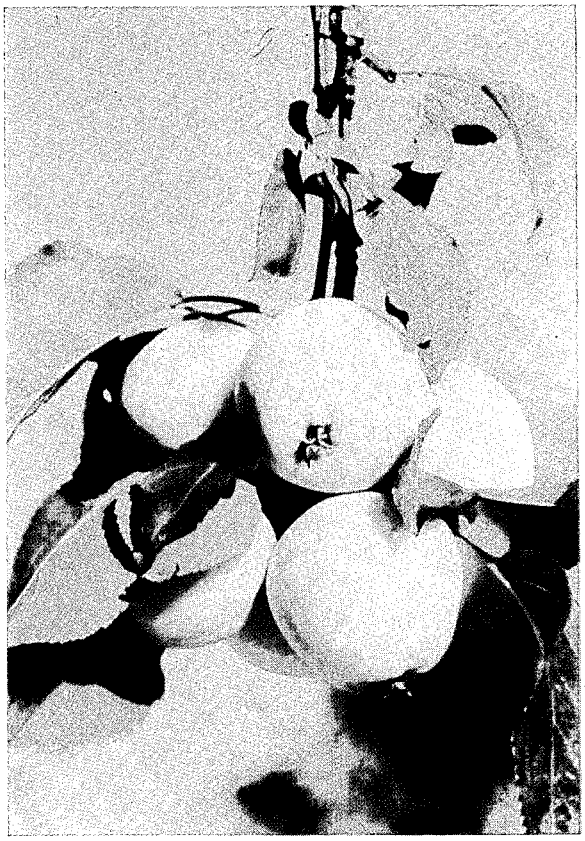
INVENTOR.
ALBERT F. ETTER.
BY
Chas. E. Townsend
ATTORNEY.

Patented June 5, 1945

Plant Pat. 658

UNITED STATES PATENT OFFICE

658

CRAB APPLE TREE

Albert F. Etter, Ettersburg, Calif., assignor to
George C. Roeding, Jr., Niles, Calif.

Application June 23, 1944, Serial No. 541,689

1 Claim. (Cl. 47—62)

This invention relates to a new variety of crab apple tree.

This new variety of crab apple tree is most nearly comparable with Transcendent, except that the fruit is two or three times as large as Transcendent.

The accompanying colored photograph illustrates this new discovery.

The following is a detail description of this new variety:

Shape: The fruit is conical in shape.
Stem: Long; up to two inches.
Calyx: Closed.
Basin: Very shallow.
Skin: Flinty, cream and pink.
Calyx tube: Medium narrow.
Core: Medium-open.
Seeds: Medium in size; brown.
Flesh: Hard and juicy; cream colored, tinted pink, showing through transparent skin.
Foliage: Large, strong and healthy.
Origin: The crab apple tree originated as a seedling of Transcendent.

A striking feature of this variety of crab apple tree in the spring is its masses of huge, fragrant flowers flushed pink. The fruit has good eating qualities far above expectancy in a variety producing such a splendid crop of flowers. The fruit matures in late fall.

What I claim is:

A new variety of crab apple tree substantially as herein disclosed, characterized by fruit which is two to three times the average size of Transcendent and has long stems, flinty transparent skin, and hard, creamy flesh showing through the transparent skin; and further characterized by its bloom of masses of huge fragrant flowers.

ALBERT F. ETTER.